US006268493B1

(12) United States Patent
Jefferson

(10) Patent No.: US 6,268,493 B1
(45) Date of Patent: *Jul. 31, 2001

(54) PREPARATION OF CELLOBIURONIC ACID FROM POLYSACCHARIDE

(75) Inventor: Richard A. Jefferson, Queanbeyan (AU)

(73) Assignee: Center for the Application of Molecular Biology to International Agriculture, Canberra (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/130,695

(22) Filed: Aug. 7, 1998

(51) Int. Cl.$^7$ .............................. C07H 1/06; C07H 13/02; C08B 37/00

(52) U.S. Cl. ................ 536/123.13; 536/114; 536/119; 536/124

(58) Field of Search .......................... 536/119, 123.13, 536/124, 114

(56) References Cited

U.S. PATENT DOCUMENTS

| | | |
|---|---|---|
| 3,891,620 | 6/1975 | Cushman et al. ............... 260/209.6 |
| 4,326,052 | 4/1982 | Kang et al. .......................... 536/1 |
| 4,326,053 | 4/1982 | Kang et al. .......................... 536/1 |
| 4,377,636 | 3/1983 | Kang et al. ........................ 435/101 |
| 4,385,123 | 5/1983 | Kang et al. ........................ 435/253 |
| 4,772,334 | 9/1988 | Hatanaka et al. .................. 127/36 |
| 4,958,016 | 9/1990 | Kerkenaar et al. .............. 536/123 |
| 5,599,670 | 2/1997 | Jefferson ............................ 435/6 |
| 5,610,037 | 3/1997 | Cros ................................ 435/104 |

OTHER PUBLICATIONS

Heidelberger and Goebel, "The Soluble Specific Substance of Pneumococcus. V. On the Chemical Nature of the Aldobionic Acid From the Specific Polysaccharide of Type III Pneumococcus," *The Journal of Biological Chemistry* 74:613–618, 1927.

Heidelberger et al., "The Soluble Specific Substance of Pneumococcus. Third Paper," *Journal of Experimental Medicine* 42:727–745, 1925.

Hotchkiss and Goebel, "Chemo–Immunological Studies on the Soluble Specific Substance of Pneumococcus," *Journal of Biological Chemistry 121*:195–203, 1937.

McGee et al., "Investigation of the Properties of Cellulose Oxidized by Nitrogen Dioxide. V. Study of Mechanism of Oxidation in Presence of Carbon Tetrachloride," *The Journal of the American Chemical Society LXIX*:355–361, 1947.

Mopper, "Improved Chromatographic Separations on Anion–Exchange Resins. II. Separation of Uronic Acids in Acetate Medium and Detection with Noncorrosive Reagent," *Analytical Biochemistry 86*:597–601, 1978.

Sømme, "Fragmentation Analysis of Extracellular Acid Polysaccharides From Seven Rhizobium Strains Part I. D–Glucuronic Acid–Containing Oligosaccharides," *Carbohydrate Research 43*:145–149, 1975.

Unruh and Kenyon, "Investigation of the Properties of Cellulose Oxidized by Nitrogen Dioxide," *The Journal of the American Chemical Society LXIV*:127–131, 1942.

Yackel and Kenyon, "The Oxidation of Cellulose by Nitrogen Dioxide," *The Journal of the American Chemical Society LXIV*: 121–127, 1942.

Goebel, "The Preparation of the Type–Specific Poly–Saccharides of Pneumococcus," *The Journal of Biological Chemistry LXXXIX*:395–398, 1930.

Goebel, "Chemo–Immunological Studies on the Soluble Specific Substance of Pneumococcus. II. The Chemical Basis for the Immunological Relationship Between the Capsular Polysaccharides of Types III and VIII Pneumococcus," *The Journal of Biological Chemistry 110*: 391–398, 1935.

Heidelberger and Goebel, "The Soluble Specific Substance of Pneumococcus. IV. On the Nature of the Specific Polysaccharide of Type III Pneumococcus," *Journal of Biological Chemistry 74*:613–624, 1927.

Kuo et al., "Identification and Location of L–Glycerate, an Unusual ACYL Substituent in Gellan Gum" *Carbohydrate Research,* 156 173–187, 1986.

Jansson et al., "Structural Studies of Gellan Gum, an Extracellular Polysaccharide Elaborated by *Pseudomonas elodea*" *Carbohydrate Research,* 124 135–139, 1983.

Kang et al., "Agar–Like Polysaccharide Produced by a Pseudomonas Species: Production and Basic Properties" *Applied and Environmental Microbiology,* vol. 43, No. 5, 1086–1091, May 1982.

Ogawa et al., "New Aldobiuronic Acid, $^{\dagger}$3–0–α–D–Glucopyranuronosyl–L–rhamnopyranose, from an Acidic Polysaccharide of *Chlorella vulgaris*" *Biosci. Biotechnol. Biochem.*, 62 (10), 2030–2031, 1998.

Heidelberger and Goebel, "The Soluble Specific Substance of Pneumococcus. IV. On the Nature of the Specific Polysaccharide of Type III Pneumococcus," *Journal of Biological Chemistry 70*:613–624, 1926.

*Primary Examiner*—Gary Geist
*Assistant Examiner*—Everett White
(74) *Attorney, Agent, or Firm*—Foley & Lardner

(57) ABSTRACT

Cellobiuronic acid may be prepared by hydrolysis of gellan. The method provides embodiments expressed in terms of amounts of cellobiuronic acid produced, amounts of gellan gum hydrolyzed and amounts of cellobiuronic acid present in fractions of a hydrolysate The method may further include isolation of a separated fraction of the hydrolysate where the separated fraction comprises cellobiuronic acid. A preferred embodiment of the method includes hydrolyzing gellan gum with a protic acid under reaction conditions that convert at least 95 wt. % of the gellan gum to a hydrolysate comprised of cellobiuronic acid and monosaccharides and isolating a separated fraction of the hydrolysate where cellobiuronic acid comprises at least a 95 wt. % of saccharides in the separated fraction.

26 Claims, No Drawings

PREPARATION OF CELLOBIURONIC ACID FROM POLYSACCHARIDE

TECHNICAL FIELD

This invention relates to a method for preparing cellobiuronic acid, and more particularly to the hydrolysis of polysaccharide to prepare a hydrolysate that includes cellobiuronic acid.

BACKGROUND OF THE INVENTION

The gene encoding β-glucuronidase has gained widespread use as a versatile tool for use in a variety of recombinant DNA techniques. The most widely embraced utility of β-glucuronidase is as a reporter gene in β-glucuronidase-deficient cells for indicating patterns of gene expression mediated by sequence elements attached to the glucuronidase gene. In addition, it has been recognized that β-glucuronidase can play a role as a positive selection marker for cells carrying exogenous DNA containing an expressible glucuronidase gene. The utility of β-glucuronidase as selective marker relies on the fact that cells cannot grow on a β-glucuronide carbon source such as a glucuronide disaccharide unless β-glucuronidase is provided to cleave the β-glucuronide bond. The most useful example of such a disaccharide is cellobiuronic acid, which comprises β-glucuronic acid in [1-4] linkage to glucose. Only cells expressing β-glucuronidase can grow on a carbon source consisting only of cellobiuronic acid.

Unlike the toxic agents commonly used in conjunction with negative selection markers in recombinant DNA techniques, cellobiuronic acid is non-toxic. Although methods related to the use of β-glucuronidase are well known, including methods for introducing β-glucuronidase genes into cells, and for assaying β-glucuronidase activity, see, e.g., U.S. Pat. No. 5,599,670 to Jefferson, there are unfortunately few economical methods for preparing cellobiuronic acid.

One known method of preparing cellobiuronic acid is by exposing cellulose to nitrous oxide. The exposure to nitrous oxide results in random oxidation of a portion of the glucose residues to glucuronic acid residues. Subsequent acid hydrolysis can be used to produce cellobiuronic acid, which may be purified from the reaction mixture. This method of preparing cellobiuronic acid is deficient for several reasons. The oxidation step involves the expense and difficulties inherent in performing a controlled oxidation in the presence of a toxic gas. Also, the physical and chemical properties of cellulose usually necessitate a pre-treatment step such as grinding, milling or steam explosion in order to allow optimal accessibility of the acid to the fibrous material during acid hydrolysis. In addition, because the oxidation step is not readily controllable, the cellobiuronic acid produced after oxidation and then hydrolysis is part of a hydrolysate mixture that may contain several byproducts such as oligo-glucuronic acids of various lengths, glucuronic acid, and some gluconic acids. These negatively charged byproducts have chemical properties similar to cellobiuronic acid, which makes purification of cellobiuronic acid by simple procedures such as anion-exchange chromatography or crystallization more difficult and expensive than if cellobiuronic acid were the only negatively charged reaction product.

The preparation of cellobiuronic acid from glucose via a synthetic oxidation approach is thus deficient for several reasons. Therefore, there is a need in the art to provide a simple method for the rapid and economical preparation of cellobiuronic acid. The present invention satisfies this need and provides other related advantages as disclosed further herein.

SUMMARY OF THE INVENTION

In one embodiment, the present invention provides a method of preparing cellobiuronic acid. The method includes the steps of exposing polysaccharide to partially hydrolyzing conditions to produce a hydrolysate that includes saccharides, where the saccharides include cellobiuronic acid; and isolating the cellobiuronic acid. The polysaccharide is formed from oxidized and nonoxidized monosaccharide residues where oxidized monosaccharide residues are not adjacent to one another, i.e., directly bonded together. In the polysaccharide, the oxidized monosaccharide residues provide at least 10% of the total number of residues.

In another embodiment, the invention provides a method of hydrolyzing polysaccharide. The method includes the step of contacting polysaccharide with a hydrolyzing agent selected from acid, base and hydrolytic enzyme, under conditions that provide a hydrolysate that includes disaccharide and monosaccharide. The disaccharide includes cellobiuronic acid, and the cellobiuronic acid is present in the hydrolysate at a concentration of at least 5 wt. % based on the total weight of polysaccharide. Preferably, the polysaccharide has not previously been subjected to oxidizing conditions such as nitric oxide oxidation.

In another embodiment, the invention provides a method of hydrolyzing g(ellan. The inventive method includes the steps of contacting gellan with an aqueous composition having a ply between 2 and 7. under conditions effective to partially hydrolyze the gellan to cellobiuronic acid, and separating the cellobiuronic acid from water.

These and other embodiments of the present invention will become evident upon reference to the following detailed description and examples. In addition, various references as identified herein which describe in more detail certain procedures or compositions (e.g., gellans, etc.), are incorporated by reference in their entireties.

DETAILED DESCRIPTION OF THE INVENTION

The present invention provides a method of preparing cellobiuronic acid from a polysaccharide. The method of the invention will be described after a brief description of cellobiuronic acid and the polysaccharides used to prepare the cellobiuronic acid.

Cellobiuronic acid is the name by which the disaccharide having the following structure (1) is commonly known:

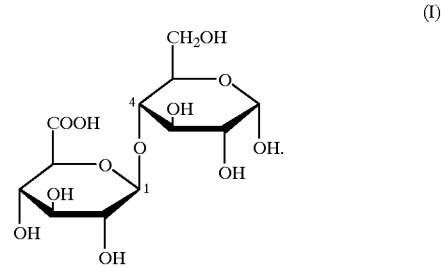

(I)

In the literature, the disaccharide of structure (I) is sometimes referred to by other names, including cellobiouronic acid, 4-O-(β-D-glucopyranuronosyl)-D-glucose, and β-glucuronosyl[1-4]glucose). See, e.g., Carbohydrates, P. M. Collins, ed. Chapman and hall, page 117, 1987. Regardless of the name, as shown in structure (I), cellobiuronic acid is a disaccharide formed between β-glucopyranuronic acid in β-linkage to a D-glucose, where the β-linkage is through carbon number 1 of D-glucopyranuronic acid and carbon number 4 of glucose (as identified in the structure (I)). A β linkage from a glucuronic acid to another sugar moiety (as seen in cellobiuronic acid) is referred to herein as a β-glucuronide linkage.

For clarity, it is noted that D-glucopyranuronic acid is a member of the uronic acid family of sugars, and is commonly known by several other names including "the pyranose form of D-glucuronic acid." Because the pyranose form of D-glucuronic acid is far more common than other forms, D-glucopyranuronic acid is often referred to simply as "D-glucuronic acid". D-glucopyranuronic acid, and saccharides containing D-glucopyranuronic acid such as cellobiuronic acid, are referred to herein as "oxidized" saccharides because they contain a carboxylic acid or carboxylic ester substituent.

The polysaccharide useful in the present invention comprises cellobiuronic residues, where a cellobiuronic acid residue is shown in structure (II). In structure (II), the wavy lines indicate attachment to adjacent saccharide residues. The term "R" in structure (II) designates either a hydrogen or an alkyl group, so that the residue of structure (II) is either a carboxylic acid or an ester, respectively. A suitable alkyl group has 1–10 carbon atoms, where the carbons may be connected in a cyclic, acyclic, linear or branched fashion. Methyl is a suitable R group. OHOH

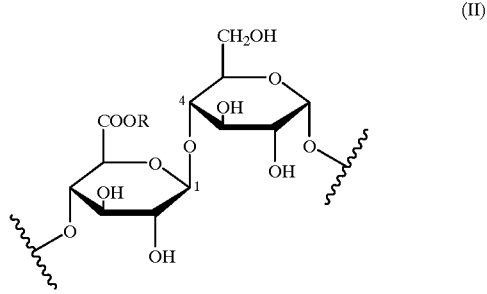

(II)

The polysaecharide useful in the invention contains a high proportion of cellobiuronic residues, and can generally be described as a high cellobiuronic acid-containing polysaecharide. More specifically, cellobiuronic residues will constitute at least 5% of the entire weight of the polysaccharide. The cellobiuronic residues will preferably constitute more than 5% of the entire weight of the polysaccharide, with preferred amounts being at least 10%, at least 25%, at least 33%, at least 50%, at least 66%. at least 75%, and 100%, including ranges bracketed by any two of these percentage values. Other monosaccharide residues in the polysaccharide may be derived from, for example, glucose, fructose, galactose, mannose and rhamanose.

The polysaceharide useful in the invention will preferably not contain adjacent oxidized monosaccharide residues. That is, two carboxylic acid or ester-substituted monosaccharide residues are preferably not directly bonded together (to one another) in the polysaccharide useful in the invention. As noted above, one disadvantage of using the oxidation product of glucose and nitrous oxide as a precursor to cellobiuronic acid is that the oxidation is very hard to control, and results in random oxidation of glucose residues such that adjacent monosaccharide residues become oxidized. The presence of adjacent oxidized monosaccharide residues in a hydrolysate renders purification of the desired cellobiuronic acid very difficult, particularly when that purification is by anion exchange chromatography. For this reason, the present invention preferably employs a polysaccharide without adjacent oxidized monosaccharide residues.

Optionally, the polysaccharide useful in the present invention has not undergone any synthetic oxidation reaction, such as nitrous oxide oxidation, prior to the hydrolysis reaction that liberates the cellobiuronic acid. Nitric oxide oxidation of glucose has been reported to generate an oxidized polysaccharide containing nitrogen.

In one embodiment, the present invention employs a polysaccharide that does not contain any nitrogen atoms.

In optional embodiments, the oxidized monosaccharide residues constitute at least 10 wt %, or at least 20 wt %, or at least 25 wt %, or at least 30 wt %, or at least 33 wt %, or at least 40 wt %, or at least 50 wt % of the monosaccharide residues present in the polysaccharide. In other optional embodiments of the present invention, at least 90 wt. %, or at least 95 wt. %, or at least 97 wt. %, or at least 99 wt. %, or 100% of the oxidized monosaccharide residues present in the polysaccharide are glucuronic acid. In other optional embodiments, at least 90 wt. %, or at least 95 wt. %, or at least 97 wt. %, or at least 99 wt. %, or 100 wt % of the glucuronic acid residues present in the polysaccharide are in β[1,4]-linkage to a glucose residue. Generally, it is desirable for all, or nearly all of the oxidized monosaccharide residues to be derived from glucuronic acid, and for all, or nearly all of the glucuronic acid residues to be in β[1-4]linkage to a glucose residue., in order to maximize the yield of purified cellobiuronic acid.

A preferred polysaccharide that may be used in the method of the invention is gellan. Gellan has been described in the literature, and certain forms of gellan are commercially available. For example, gellan is described in Kennedy, J. F., *Carbohydrate Chemistry*, page 630 (1988) Clarendon Press, Oxford, as an extracellular anionic polysaccharide produced by the bacterium *Pseudomonas eloclea* (ATCC 31461). According to Kennedy, gellan from this source is a partially O-acetylated linear polymer of D-glucose, L-rhamanose, and D-glucuronic acid, which has the basic repeating unit, excluding acetyl groups, of →3)-β-D-Glcp-(1→4)-β-D-GlcpA-(1→4)-β-D-Glcp-(1→4)-α-L-Rhap-(1→, which may also be written as GlcA 1-4 Glu 1-4 Rha 1-3 Glu, where "GlcA" represents glucuronic acid, "Glu" represents glucose and "Rha" represents rhamanose. In gellan. 33% of the monosaccharide residues are oxidized monosaccharide residues, and cellobiuronic residues constitute 66 wt % of the monosaccharide residues in the polysaccharide.

Gellan is also described in Aspingall (*The Polysaccharides*, vol. 2, Academic Press, 1983, page 479) as obtained from *Pseudomonas elodea* and contains a glucose:rhamanose ratio of 2:1. Aspingall states that gellan could be obtained from Kelco, Division of Merck & Co., Inc. as PS-60. PS-60 is available in three grades: (a) "native", which contains 11% uronic acid, 3% acetylated uronic acid. 10% protein. 7% ash, and a 2:1 ratio of glucose to rhamanose; (b) "deacetylated", which contains 13% uronic acid, no acetylated uronic acid, 17% protein and 8% ash, with a 2:1 ratio of glucose to rhamanose; and (c) "dcacetylated and clarified", which contains 22% uronic acid, no acetylated uronic acid, 2% protein, 9.5% ash, and a 2:1 ratio of glucose to rhamanose. "Clarified" gellan is described below.

Gellan is also described in the following references: U.S. Pat. Nos. 4,326,052: 4,326,053; 4,377,636, and 4,385,123. Other descriptions of gellan may be found in, for example, Jansson et al., *Carbohydr. Res.* 124, 135, 1983; and Sanderson et al. *Progress in Food and Nutrition Science,* vol. 7, (eds. G. O. Phillips, et al.) p. 201, Pergamon Press, Oxford, 1984.

Certain gellans are currently commercially available, and a preferred gellan of the present invention is known commercially as GELRITE™. GELRITE™ is derived from a naturally occurring polysaccharide after deacetylation and "clarification", where clarification refers to a process wherein polypeptide is fully or partially removed from the polysaccharide. GELRITETM is available from a variety of sources including, for example, Sigma Chemical Co., St. Louis, Mo. Essentially the same material is also available from Sigma Chemical under the tradename PHYYTAGAR™.

Gellan selected from native gellan gum, clarified gellan gum, deacetylated gellan gum, or in a preferred embodiment, gellan gum that is both clarified and deacetylated, and the like may be used in the present invention. Thus, gellan as used in the present invention is a polysaccharide that incorporates repeating residues derived from the disaccharide cellobiuronic acid or derivatives of cellobiuronic acid such as acetylated cellobiuronic acid or esterified cellobiuronic acid. Furthermore, and of importance to the present invention, gellan does not contain any oxidized monosaccharide residues except those derived from glucuronic acid, and the oxidized residues are not adjacent to one another (i.e., not bonded together) in the polysaccharide.

The present invention provides a method of preparing cellobiuronic acid wherein polysaccharide (e.g., gellan) is hydrolyzed to produce a hydrolysate that includes saccharides including cellobiuronic acid. When the polysaccharide is gellan, the saccharides will also include glucose and rhamanose. At least some of the cellobiuronic acid is then isolated from the other saccharides. The hydrolysis conditions are selected with a view toward optimizing the amount of cellobiuronic which is formed. Thus, the hydrolyzing agent, time, temperature, reagent and reactant concentrations, and other features of the hydrolysis reaction are preferably selected in order to achieve a high yield of cellobiuronic acid. It should be noted that the hydrolysis conditions of the invention are only "partially hydrolysing" in order that the disaccharide cellobiruonic acid is not hydrolyzed to monosaccharides.

The extent of hydrolysis can be measured and described in several ways. A convenient description is in terms of the amount of disaccharide present in the hydrolysate. As discussed below, and in comparison to other disaccharides that may be obtained from the polysaccharide, cellobiuronic acid is particularly resistant to hydrolysis. Thus, in the practice of the present invention, it is desirable to maximize the amount of disaccharide present in a hydrolysate. The present invention provides a method wherein the hydrolysate contains at least 20 wt. % disaccharide based on the total weight of saccharide present in the hydrolysate. As used herein, "the total weight of saccharide" refers to the total weight of mono-, di-, oligo-, and polysaccharides present in the hydrolysate. When deacetylated and clarified gellan is used as the starting polysaccharide, the "total weight of saccharide" will essentially equal the weight of gellan used in the hydrolysis reaction.

Optionally, the hydrolysate contains more than 20 wt. % disaccharide, and may contain at least 30 wt. % or at least 40 wt. % or at least 50 wt. % disaccharide, or at least 66 wt. %, or at least 75 wt. %, or 100 wt % based on the total weight of saccharide in the hydrolysate. As explained above, native and other "non-clarified" gellans contain a protein residue, and thus will afford a lower yield of cellobiuronic acid, if the yield is based on the weight of such a gellan. Thus, in terms of the gellan itself, the invention provides that the hydrolysate contains at least 10 wt. % disaccharide, and more preferably contains at least 20 wt. %, or at least 30 wt. %, or at least 40 wt. %, and more preferably at least 50 wt. % or at least 60 wt. % disaccharide.

It is preferred not to hydrolyze the gellan too extensively, or else the cellobiuronic acid is converted into monosaccharides. The total of the monosaccharides and disaccharides in the hydrolysate after the partial hydrolysis is preferably at least 50 wt. %, more preferably at least 70 wt. %. and still more preferably at least a 90 wt. %, based on the total weight of the saccharides in the hydrolysate, eased on the weight of the starting polysaccharide, the total of the monosaccharides and disaccharides in the hydrolysate after the partial hydrolysis is preferably at least 50 wt. %, more preferably at least 70 wt. %, and still more preferably at least 90 wt. %.

Alternatively, the amount of hydrolysis may be expressed by a weight fraction of oxidized disaccharide present in a fraction that contains oxidized saccharides provided by the hydrolysis. Typically, the hydrolysis reaction will convert any ester groups present in the polysaccharide into carboxylic acid groups. The carboxylic acid groups will be "anionic" in the sense that they bear a negative charge under basic conditions. Thus, the hydrolysate may be characterized in terms of its content of anionic saccharide.

After the hydrolysis reaction, the hydrolysate may be eluted through an anion exchange resin to separate carboxylic acid-containing ("anionic") saccharides from nonionic saccharides. The weight of the separated anionic saccharides is the weight of the "anionic saccharides fraction". The content of the anionic saccharides fraction may then be determined, in terms of wt. % monosaccharides, disaccharides, etc., using an LC (liquid chromatography) detector, which examines the fraction by, for example, refractive index. The present invention provides a method wherein at least 50 wt. % of the anionic saccharide fraction is disaccharide, preferably at least 80 wt. % is disaccharide, and more preferably at least 95 wt. % of the anionic saccharides fraction is disaccharide. Preferably, the disaccharide in the anionic fraction is entirely, or nearly entirely cellobiuronic acid, so that the present invention provides a method wherein at least 50 wt. % of the anionic saccharides fraction is cellobiuronic acid, preferably at least 80 wt. % is cellobiuronic acid, and more preferably at least 95 wt. % of the anionic saccharides fraction is cellobiuronic acid.

The content of the hydrolysate may be determined by any of several methods known in the art. One convenient method is liquid chromatography, wherein the hydrolysate is injected onto a chromatography column that discriminates on the basis of molecular weight, and a detector analyzes the eluent as a function of time. These types of chromatography devices are commercially available from, e.g., Water Associates and Hewlett-Packard.

A preferred hydrolysis reaction of the present invention employs 100 wt. % of deacetylated and clarified gellan and provides a hydrolysate that contains 50 wt. % cellobiuronic acid and 50 wt. % monosaccharides, which are typically glucose and rhamanose. However, the invention also provides methods wherein gellan is either under-hydrolyzeds or over-hydrolyzed with respect to the preferred hydrolysis reaction. Under-hydrolysis provides for anionic saccharides other than cellobiuronic acid, which include glucuronide-containing oligosaccharides of three or more residues. In over-hydrolysis, the anionic saccharides include glucuronic acid. This difference in compositions of the anionic saccharides resulting from under-hydrolysis or over-hydrolysis provides a basis to test and adjust hydrolysis conditions so as to approach the preferred hydrolysis reaction.

Thus, the hydrolysate may be fractionated on the basis of charge. That is, the anionic saccharides may be separated from the nonionic saccharides, using, for example, anion exchange chromatography or precipitation methods. Then the fraction containing the anionic saccharides may be analyzed in terms of molecular weight, using, for example, liquid chromatography as described above, and the relative amounts of anionic monosaccharide, disaccharide, trisaccharide, etc. determined. Multiple reactions may be run, under various reaction condition, in order to identify the preferred set of reaction conditions to produce a high yield of anionic disaccharide, which is cellobiuronic acid.

In general, the only anionic saccharides that may be present in gellan and hydrolysis products thereof are glucuronic acid, cellobiuronic acid and oligosaccharides of three or more residues where at least one residue is glucuronic acid. Various methods are well known for assessing the relative amounts of these anionic species, as well as for distinguishing glucuronic acid from glucuronide oligosaccharides. These methods include, but are not limited to, reaction with napthorescorcinol, reaction with bicinchoninate reagent, potassium iodide oxidation, reaction with carbazole, decarboxylation with hydrochloric acid and combinations of these and other reactions. Similarly, there are a variety of methods for analyzing the neutral saccharide content of a sample. Such methods may be used alone or in combination with other methods for analyzing saccharides in order to identify and quantify the anionic species and other saccharides resulting from the hydrolysis of gellan.

There are also numerous methods known to those of ordinary skill in the art for analyzing the saccharide content of a hydrolysate mixture by separation techniques. Among the most common methods are thin layer chromatography, paper chromatography, paper electrophoresis, high pressure liquid chromatography (HPLC), analytical ion exchange chromatography, gas chromatography, mass spectroscopy, and combinations thereof. Use of any one or more of these methods may be employed in a simple test for identifying suitable reaction conditions for the preparation of cellobiuronic acid according to the present invention. An example of such a test is an anion exchange procedure that yields a broad separation of cellobiuronic acid from monouronic acids and other anionic saccharides, as described by *Moopper Separation of Uronic Acids in Acetate Medium and Detection with a Noncorrosive Reagent, Analyt. Biochem.* 86, 597–601 (1978). Other suitable tests may be found in, e.g., *Methods in Plant Biochemistry, Vol.* 2, Carbohydrates, P. M. Dey and J. B. Harborne Academic Press (1990).

Suitable methods that may be used to test for the presence of glucuronides in particular may be found in, for example, *Glucuronic Acid, Free and Combined, Chap.* 1, *Section V, Separation of Uronic Acids,* G. Dutton, Academic Press (1966). In addition, a variety of procedures applicable to the separation of saccharides may be readily obtained from vendors of chromotography media and equipment such as BioRad, Sigma, Waters, Pharmacia and others. Any procedure that allows quantitative estimation of saccharide reaction products in a hydrolysate may be used to optimize reaction conditions to achieve a hydrolysate of the present invention. Such procedures may be made particularly useful for the present invention when they are calibrated with standards representing expected anionic hydrolysis products of gellan gum, which may include, for example, glucuronic acid, cellobiuronic acid, and glucuronide oligosaccharides of three or more residues.

An important feature of the hydrolysis reaction of the present invention is the selection of the hydrolyzing agent. Preferred hydrolyzing agents should cleave the bond between adjacent monosaccharide residues, while retaining the integrity of the monosaccharides themselves. Preferred hydrolyzing agents include protic acid and hydrolytic enzymes. For embodiments using a hydrolytic enzyme, any of a variety of known hydrolytic enzymes may be used. The enzyme should be capable of hydrolyzing both a β-glucosyl-glucose bond and a β-glucosyl-glucuronic acid bond, but is preferably not capable of hydrolyzing the β-glucuronosyl-glucose bond of cellobiuronic acid. One useful resource for finding suitable enzymes is the annually updated publication *Carbohydrate Chemistry-Specialist Periodical Reports, Vols.* 4–15, *Part II, Chapter* 6, J. F. Kennedy, (1971 onward). Suitable enzymes include, without limitation, cellulases, cellobiohydrolases, β-glucosidases, glucoamylases and glucanses. Enzymes and techniques that may be used to hydrolyze gellan are disclosed in, for example, U.S. Pat. No. 4,958,016. As discussed above, suitable hydrolysis reaction conditions may be determined by analysis of hydrolysis products using methods known to those of skill in the art.

In a preferred embodiment, the hydrolyzing agent is at least one protic acid. The protic acid may be selected from a mineral acid and an organic acid, and may be used to provide a composition at a pH between 2 and 7 that includes gellan and water. Suitable protic acids include, but are not limited to, mineral acids such as hydrochloric acid, sulfuric acid, phosphoric acid, and hydrofluoric acid; and organic acids such as trifluoroacetic acid and alkyl or aryl-sulfonic acids. In a preferred embodiment of the invention, the protic acid is sulfuric acid or an alkyl-sulfonic acid. General reaction conditions for polysacchande hydrolysis using alkyl-sulfonic acids may be found in, for example, U.S. Pat. No. 3,901,874.

As noted above, the difference in acid lability between the glucuronide bond and other glycosidic bonds in gellan can be exploited in order to optimize the amount of cellobiuronic acid present in the hydrolysate. Glycosidic bonds between sugar residues in a polysaccharide vary greatly in susceptibility to acid hydrolysis with an order of increasing acid stability of furanoside<pyranoside<deoxyhexoside<hexoside<uronoside (Stephans et al., *Methods in Plant Biochemistry, vol.* 2 *Carbohydrates,* p. 496). Gellan consists of both uronoside and pyranoside bonds while cellobiuronic acid has only a uronoside bond, allowing hydrolysis of gellan under conditions that cleave essentially all pyranoside bonds and leave intact essentially all uronoside bonds. In the practice of the present invention, reaction conditions for the hydrolysis of gellan may be found that most optimally exploit the different acid labilities between the pyranoside bonds of gellan gum and the uronoside bond of cellobiuronic acid.

In addition to the identity of the hydrolyzing agent, other reaction conditions such as gellan concentration, concentration of hydrolyzing agent, temperature, pressure and reaction time may be selected so as to provide the amount of hydrolysis described in various embodiments of this invention. These reaction conditions are interdependent, and a suitable set of reaction conditions may be readily determined while monitoring the hydrolysis reaction by techniques described herein so as to provide a desirable hydrolysate.

In another aspect of this invention, any of the methods described above may further include isolating a separated fraction of the hydrolysate wherein the separated fraction includes cellobiuronic acid. One embodiment of this method includes preparing cellobiuronic acid by hydrolyzing a gellan with a protic acid to produce a hydrolysate under reaction conditions wherein at least 5 wt. % of the gellan (glum is converted to cellobiuronic acid and subsequently isolating a separated fraction of the hydrolysate, wherein the separated fraction includes cellobiuronic acid. In one embodiment, at least 50 wt. % of saccharidess in the separated fraction are cellobiuronic acid, while in more preferred embodiments, cellobiuronic acid constitutes at least 80 wt. %, or at least 95 wt. % of the saccharidess in the separated fraction.

In still other embodiments, at least 20 wt. % of the gellan gum is converted to cellobiuronic acid and at least 80 wt. % of saccharides in the isolated fraction is cellobiuronic acid. In a more preferred embodiment, at least 40 wt. % of the gellan glum is converted to cellobiuronic acid and at least 95 wt. % of saccharides in the isolated fraction is cellobiuronic acid. In a more preferred embodiment, about 50 wt. % of the gellan gum is converted to cellobiuronic acid and at least 98 wt. % of saccharides in the isolated fraction of the hydrolysate is cellobiuronic acid.

In another embodiment, the invention provides a method of hydrolyzing polysaccharide which includes the step of contacting polysaccharide with a hydrolyzing agent selected from acid, base and hydrolytic enzyme, under conditions that provide a hydrolysate which will contain disaccharide and monosaccharide. The disaccharide includes cellobiuronic acid, and the cellobiuronic acid is present in the hydrolysate at a concentration of at least 5 wt. % based on the total weight of polysaccharide. The polysaccharide has preferably not previously been subjected to oxidizing conditions, such as nitric oxide oxidation.

The isolation of a separated fraction of the hydrolysate may be accomplished by standard techniques. Suitable techniques include at least one of chromatography, crystallization and precipitation. As used herein, chromatography includes all methods known in the art for separating compounds by differential partition between a stationary and a mobile phase. Examples include, but are not limited to, thin layer chromatography, size exclusion chromotography, ion chromotography, liquid chromotography, gas chromotography, paper chromotography, and electrophoresis. As used herein, the term precipitation refers to the formation of an insoluble composition from a solution that includes dissolved solutes. As used herein, the term crystallization refers to a type of precipitation, where crystallization provides for an insoluble composition that is at least partly in the form of crystals.

In one embodiment, the isolation of a separated fraction of the hydrolysate is accomplished by anion exchange chromatography. In another preferred embodiment, isolation is accomplished by crystallization. In another embodiment, isolation is accomplished by precipitation. In still other embodiments, isolation is accomplished by a procedure that includes a combination of at least two of chromatography, crystallization and precipitation.

In embodiments of the present invention that include isolating a separated fraction by anion exchange chromatography, a preferred isolation procedure is to contact the hydrolysate mixture with an anion exchange media to form a bound fraction containing cellobiuronic acid, and an unbound fraction. The media may be washed with a wash solution that removes the unbound fraction, and then cellobiuronic acid is eluted from the anion exchange media by contacting the same with an elution solvent containing a substitute anion. The cellobiuronic acid may then be recovered from the elution solvent by crystallization, evaporation, precipitation or other conventional technique. In this way, an anionic fraction that includes cellobiuronic acid is isolated from a neutral fraction that contains one or more monosaccharides. Any of crystallization, evaporation or precipitation may be used to provide the cellobiuronic acid in a solvent-free form.

There are many available anion exchange media suitable for the practice of this invention, for example, those contained in the list of anion exchange resins supplied by Sigma Chemical Company under the heading "Chromatography, Ion Exchange" in their catalog. It is preferred, but not necessary that the anion exchange media be one known or characterized as a "weakly basic" anion exchanger rather than a "strongly basic" exchanger because strongly basic resins may cause unwanted reactions with bound species, such as additional hydrolysis or decomposition into smaller organic molecules. It is also preferred that the anion exchange resin be inexpensive, easy to manipulate and easy to regenerate.

A preferred embodiment of the present invention employs an anion exchanoe resin such as Amberlite™ IRA 96 or Dowex™ 66. each having polyamine functional groups attached to a polystyrene resin. Many procedures operated in batch or by column containment can be designed for isolating a cellobiuronic acid-containing fraction using anion exchange procedures.

In embodiments of the present invention that employ isolating a separated fraction by crystallization or precipitation, any of several procedures familiar to those of skill in the art may be employed. In the case of reaction conditions which may be characterized as under-hydrolysis, isolating a separated fraction may include a first step of precipitating an oligosaccharide fraction. A common method for precipitation of an oligosaccharide fraction is by the addition of 2 to 20 volumes of a water miscible organic solvent to I volume of a hydrolysate, followed by centrifugation, filtration or other method of collecting the precipitate. Typical water miscible solvents include, but are not limited to ethanol, propanol, and acetone.

In cases where precipitation of oligosaccharide fraction is desired, the pH of the hydrolysate, and an amount of water miscible solvent, can each be selected in order to maximize the precipitation of oligosaccharides having three or more residues, and minimize the precipitation of cellobiuronic acid. Typically in such cases, the hydrolysate is adjusted to a pH which will cause a fraction of glucuronide residues to acquire a partial anionic charge so that, upon addition of the polar organic solvent, neutral oligosaccharides and partially charged oligosaccharides of greater than three residues will preferentially precipitate with respect to cellobiuronic acid. Similarly, the amount of polar organic solvent added may be adjusted to optimize the preferential precipitation. Typically, 2 to 10 volumes of polar organic solvent will preferentially precipitate oligosaccharides of greater than three residues. Precipitation conditions may be tested by the same types of procedures as described above, but applied to testing the saccharide content of the precipitate and the supernatant that remains.

When precipitating an oligosaccharide fraction is used as a first step toward isolating a separate fraction, a subsequent step may include chromatography or a further precipitation or crystallization of cellobiuronic acid. In one embodiment, precipitation of cellobiuronic acid may also be accomplished by the use of a pH adjustment and a water miscible organic solvent, as described above. In a preferred embodiment, the pH of the solution containing cellobiuronic acid may be adjusted so as to neutralize the charged on glucuronide residues, and 5 to 20 volumes of the polar organic solvent are added to one volume of a solution containing cellobiuronic acid.

Other methods of precipitation or crystallization may be employed in the practice of this invention. In some embodiments, precipitation or crystallization may comprise as a single step of isolating a separated fraction comprising cellobiuronic acid. In other embodiments, precipitation or crystallization may comprise a step subsequent to one or more prior steps, where the prior steps may be chromatography, precipitation or crystallization of a saccharides fraction.

In one embodiment, precipitation or crystallization is accomplished by the addition of a precipitating agent directly to the hydrolysate obtained after hydrolysis. The precipitating agent may be a salt of an alkali or alkaline earth metal. In another embodiment the precipitating agent may be a cetyltrimethylammonium halide or a cetyl pyridinium halide. In a preferred embodiment, the precipitating agent is selected from a hydroxide agent of barium, calcium, and magnesium. In a more preferred embodiment, the precipitating agent is barium hydroxide.

The methodology described herein is useful for the preparation of cellobiuronic acid from polysaccharide on a large (e.g., industrial) scale, so that commercial, i.e., multi-gram quantities of cellobiuronic acid may be economically prepared. For example, it is possible to provide a hydrolysate comprising at least 100 grams of cellobiuronic acid, or at least 1,000 grams of cellobiuronic acid, according to the present invention. Thus, the present invention provides methodology for isolating hundreds or even thousands of grams of cellobiuronic acid essentially free from monosaccharides such as rhamnose and glucose. As used herein, "essentially free" means that the cellobiuronic acid constitutes at least 95%, preferably at least 98%, more preferably at least 99%, still more preferably at least 99.5% of the entire weight of the cellobiuronic acid +monosaccharides, where these weight percent values may be determined by calibrated liquid chromatography.

One of ordinary skill in the art will recognize variations in the methodology of this invention that may also accomplish the preparation of cellobiuronic acid from polysaccharide. Accordingly, the following examples are presented for purposes of illustration, not limitation.

EXAMPLES

Example 1

Determining Hydrolysis Conditions for Preparation of Cellobiuronic Acid from Gellan Gum by Hydrolysis with Sulfuric Acid A solution of 2.5% deacetylated and clarified gellan is prepared by dissolving 2.5 grams of GelRite™ in 100 ml of water and heating to 100° C. for 5 minutes. A 5 ml sample of the resulting solution is dispensed into 8 reaction tubes, each containing 5 ml of sulfuric acid at different concentrations representing a two fold dilution series from 64% to 1% v/v giving final reaction concentrations in the range of 32% to 0.5%. The reaction tubes are sealed, reflux boiled for I hour, then cooled to room temperature to form a hydrolysate mixture. Aliquots of each hydrolysate mixture are applied to a Lichrosorb™-NH, HPLC column (Merck Corp.), and the column is developed in a solution of acetonitrile/H$_2$O (80:20 v/v). The elution characteristics of the column may be previously characterized using calibration standards containing the neutral monosaccharides glucose, rhamanose, and the anionic saccharides glucuronic acid, cellobiuronic acid, glucuronosyl-glucosyl-rhamanose, glucuronosyl-glucosyl-rhamanoyl-glucose and an unhydrolyzed sample of GelRite™.

Quantitative assessment of the reaction conditions is made by comparing the elution profiles of products obtained from each reaction condition to a profile obtained from calibration standards. Samples from the elution profile are also analyzed for uronic acid content by the carbazole method.

Example 2

Hydrolysis of Gellan Gum and Isolation of a Separated Fraction Containing Cellobiuronic Acid by Anion Exchange Chromotography A hydrolysate is prepared by hydrolyzing 1.0 gram of deacetylated and clarified gellan gum in 50 ml of 10% sulfuric for I hour with reflux boiling. The hydrolysate is diluted 20-fold with water and the pHf adjusted to about 7 by titration with ammonium hydroxide in the presence of an indicator dye. The supernatant is mixed and applied to a column containing 10 g of Dowex 66 (Sigma Chemical Corp.) pre-equilibrated with 0.05 M ammonium acetate pH 7. The column is washed with 100 ml of 0.05 M ammonium acetate pH 7 to remove unbound components. The column is then eluted with 50 ml of 0.15 N acetic acid. The eluent is titrated with a solution of barium hydroxide until the mixture is just acidic to phenylphthalein. Approximately 450 ml of ethanol is added to the titrated mixture, and a precipitate is formed after standing for 30 min. The precipitate is recovered by filtration and dried.

Example 3

Hydrolysis of Gellan Gum with Sulfonic Acid and Isolation of a Fraction Containing Cellobiuronic Acid Five grams of a silica gel ("Cab-O-Sill", grade H-5, Cabot Company) is thoroughly mixed with 95 grams of dry deacetylated and clarified gellan. To this is sprayed 20 ml of an isopropanol Solution containing 5 g of dissolved alkyl-benzene sulfonic acid ("Conoco" SA-597, technical grade). The mixture is vigorously stirred during addition of the spray. The isopropanol is evaporated, and the dried composition is ball-milled for 30 minutes to thoroughly pulverize agglomerate particles. The pulverized material is added to a pressure vessel, and heated to 100° C. for 8 hours to form a hydrolysate. The hydrolysate is dissolved in 1000 ml of water and filtered to remove insoluble materials. The filtered material is mixed with 3 liter of ethanol and allowed to stand until a precipitate forms. The precipitate is isolated by filtration and a second filtrate is recovered. The pH of the second filtrate is adjusted to a pi I of about 7 with barium hydroxide. The pH adjusted filtrate is then mixed with an additional 13 liter of ethanol and allowed to stand until a second precipitate forms. The second precipitate is recovered by filtration and redissolved in 500 ml of water. This solution is mixed with of 8 liter of methanol until insoluble crystals form. The crystals are recovered by filtration and dried.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

What is claimed is:

1. A method of preparing cellobiuronic acid comprising:
   exposing gellan gum to partially hydrolyzing conditions to produce a hydrolysate comprising anionic saccharides, the anionic saccharides comprising at least 50 wt. % cellobiuronic acid; and
   isolating the cellobiuronic acid by anion exchange chromatography.

2. The method of claim 1 wherein the anionic saccharides comprise at least 80 wt. % cellobiuronic acid.

3. The method of claim 1 wherein the anionic saccharides comprise at least 95 wt. % cellobiuronic acid.

4. The method of claim 1 wherein the gellan gum is clarified gellan gum.

5. The method of claim 1 wherein the gellan gum is deacetylated gellan gum.

6. The method of claim 1 wherein acid hydrolysis is used to produce the hydrolysate.

7. The method of claim 1 wherein the hydrolysate comprises about 30 to about 60 wt. % disaccharide based on the total weight of saccharides in the hydrolysate.

8. The method of claim 1 wherein the hydrolysate comprises about 40 to about 50 wt. % cellobiuronic acid based on the total weight of saccharide in the hydrolysate.

9. The method of claim 1 wherein the hydrolysate comprises at least 70 wt. % monosaccharide and disaccharide, based on the total weight of saccharide in the hydrolysate.

10. The method of claim 1 wherein the hydrolysate comprises at least 60 wt. % of monosaccharide and disaccharide, based on the total weight of gellan gum.

11. The method of claim 1 wherein the hydrolyzing produces a hydrolysate comprising at least 100 grams of cellobiuronic acid.

12. The method of claim 1 wherein the hydrolyzing produces a hydrolysate comprising at least 1,000 grams of cellobiuronic acid.

13. The method of claim 1 wherein the isolation provides a separation of disaccharide from both monosaccharide and oligosaccharide.

14. The method of claim 1 wherein the isolation further comprises precipitation.

15. The method of claim 1 wherein the isolated cellobiuronic acid is essentially free from glucose.

16. The method of claim 1 wherein at least 100 grams of cellobiuronic acid is isolated.

17. A method of hydrolyzing gellan gum comprising
   (a) contacting gellan gum with a hydrolyzing agent selected from the group consisting of acid, base and hydrolytic enzyme, under conditions that provide a hydrolysate comprising anionic saccharides, the anionic saccharides comprising at least 50 wt. % cellobiuronic acid, where the cellobiuronic acid is present in the hydrolysate at a concentration of at least 5 wt. % based on the total weight of gellan gum, and wherein the gellan gum has not previously been subjected to oxidizing conditions; and
   (b) isolating an anionic fraction comprising cellobiuronic acid from a neutral fraction comprising one or more monosaccharides using anion exchange chromatography.

18. The method of claim 17 wherein the gellan gum is selected from the group consisting of native gellan gum, clarified gellan gum, deacetylated gellan gum and gellan gum that is both clarified and deacetylated.

19. The method of claim 17 wherein the hydrolysate comprises at least 20 wt. % cellobiuronic acid based on the total weight of gellan gum.

20. The method of claim 17 wherein the hydrolysate comprises at least 100 grams of cellobiuronic acid.

21. The method of claim 17, further comprising separating cellobiuronic acid from monosaccharide.

22. The method of claim 17, further comprising isolating an anionic fraction comprising cellobiuronic acid from a neutral fraction comprising one or more monosaccharides.

23. The method of claim 17 further comprising separating monosaccharide and disaccharide from other saccharide species present in the hydrolysate.

24. The method of claim 17 further comprising separating monosaccharide from disaccharide, wherein the disaccharide comprises cellobiuronic acid.

25. The method of claim 17, further comprising isolating cellobiuronic acid in a solvent-free form.

26. A method of hydrolyzing gellan gum comprising contacting gellan gum with an aqueous composition having a pH between 2 and 7, under conditions effective to partially hydrolyze the gellan to form a hydrolysate comprising anionic saccharides, the anionic saccharides comprising at least 50 wt. % cellobiuronic acid, isolating the cellobiuronic acid from neutral saccharides by anion exchange chromatography, and separating the cellobiuronic acid from water.

* * * * *